(12) United States Patent
Vermaak

(10) Patent No.: US 7,585,293 B2
(45) Date of Patent: Sep. 8, 2009

(54) URINE COLLECTION APPARATUS

(75) Inventor: Jan Christiaan Vermaak, Somerset West (ZA)

(73) Assignee: Onkologie Internasionale Beleggings (Proprietary) Limited, Stellenbosch, Cape Province (ZA)

( * ) Notice: Subject to any disclaimer, the term of this patent is extended or adjusted under 35 U.S.C. 154(b) by 0 days.

(21) Appl. No.: 10/994,254

(22) Filed: Nov. 23, 2004

(65) Prior Publication Data

US 2006/0111648 A1    May 25, 2006

(51) Int. Cl.
*A61F 5/44* (2006.01)
*A61M 1/00* (2006.01)

(52) U.S. Cl. .................. 604/329; 604/317; 604/327; 604/334

(58) Field of Classification Search .................. 604/329, 604/317, 327, 334; 600/574
See application file for complete search history.

(56) References Cited

U.S. PATENT DOCUMENTS

| | | | | |
|---|---|---|---|---|
| 4,610,675 A | * | 9/1986 | Triunfol | ..................... 604/329 |
| 5,004,463 A | * | 4/1991 | Nigay | ..................... 604/329 |
| 6,299,606 B1 | * | 10/2001 | Young | ..................... 604/329 |
| 6,398,742 B1 | * | 6/2002 | Kim | ..................... 600/574 |

\* cited by examiner

*Primary Examiner*—Jacqueline F. Stephens
(74) *Attorney, Agent, or Firm*—Birch, Stewart, Kolasch & Birch, LLP

(57) ABSTRACT

Urine collection apparatus is provided which can be used to assist bedridden and/or incontinent patients, particularly female patients. The apparatus includes a urine collector which is shaped for location against the perineal region of a patient adjacent the urethra. The urine collector comprises a hollow body having opposed ends in which an inlet for air and an outlet for air and urine are formed, respectively. The body has a central region between the end regions with a reduced cross-sectional area. This effectively creates a venturi adjacent the patient's urethra when air passes through the collector. The apparatus includes a urine receptacle with an inlet for receiving air and urine from the collector, and an outlet for air which is connectable to a source of low pressure. The source of low pressure will typically be an impeller driven by an electric motor, which creates a sufficiently strong air flow through the apparatus to entrain urine and transport it to the receptacle.

16 Claims, 2 Drawing Sheets

URINE COLLECTION APPARATUS

BACKGROUND OF THE INVENTION

THIS invention relates to urine collection apparatus.

When a patient is bedridden and/or incontinent, urination may be problematic. Depending on the patient's condition, it may be difficult to urinate without assistance.

It would be desirable to provide an apparatus which would assist a bedridden patient to urinate without assistance, at any time.

SUMMARY OF THE INVENTION

Urine collection apparatus comprising:
  a urine collector shaped for location against the perineal region of a patient adjacent the urethra, the urine collector having an inlet for air and an outlet for air and urine; and
  a urine receptacle having an inlet for receiving air and urine from the urine collector, and an outlet for air which is connectable to a source of low pressure, so that air passing through the inlet of the urine collector entrains urine for delivery to the urine receptacle.

The urine collector is preferably shaped to define a venturi between the inlet and the outlet thereof, the venturi being locatable directly adjacent the patient's urethra when the urine collector is correctly located.

The urine collector may be shaped for use by a female patient.

The urine collector may comprise a hollow body having opposed ends in which the inlet and the outlet are formed, the urine collector having first and second end regions and a central region between the end regions having a cross sectional area less than that of the end regions.

The urine collector is preferably formed from a flexible plastics material.

The apparatus preferably includes a source of low pressure in the form of an impeller or pump arranged to apply suction to the outlet of the urine collector when the inlet of the urine receptacle is connected to the outlet of the urine collector, thereby to cause an airflow through the urine collector.

The source of low pressure may comprise an impeller arranged to be driven by an electric motor and located in a housing, the urine receptacle being locatable in an opening defined in the housing so that the outlet of the urine receptacle is in communication with an air inlet of the impeller.

The invention extends to a urine collector suitable for use with the above defined apparatus, the urine collector being shaped for location against the perineal region of a patient adjacent the urethra and comprising a hollow body defining an inlet for air and an outlet for air and urine.

Preferably, the body is shaped to define a venturi between the inlet and the outlet thereof, the venturi being locatable directly adjacent the patient's urethra when the urine collector is correctly located.

The body preferably has opposed ends in which the inlet and the outlet are formed, the urine collector having first and second end regions and a central region between the end regions having a cross sectional area less than that of the end regions.

The body may be formed from a flexible plastics material.

DESCRIPTION OF EMBODIMENTS

Figure 1:
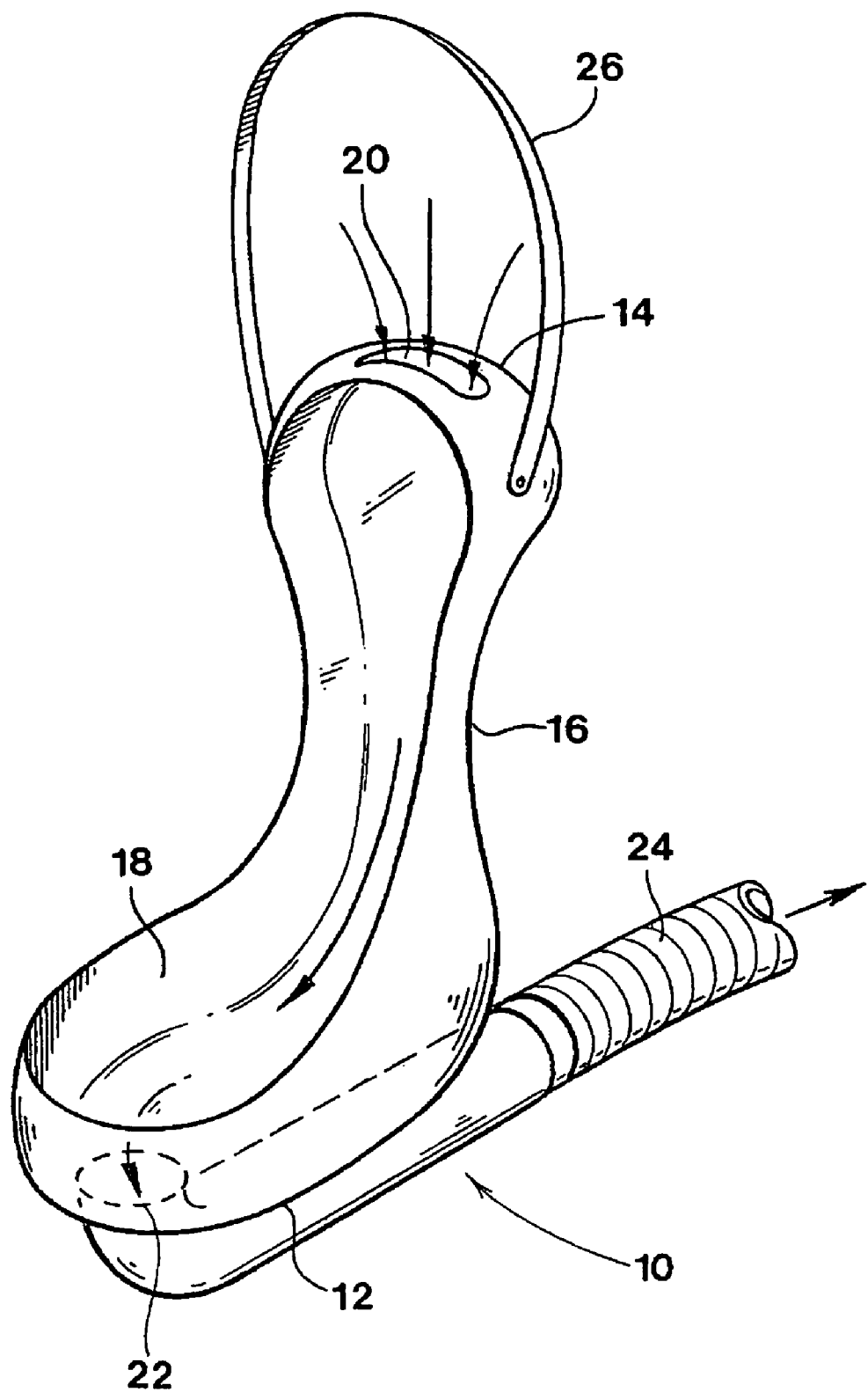
FIG. 1 is a pictorial view of a urine collector forming part of urine collection apparatus according to the invention.

FIG. 1 shows a urine collector of the invention which comprises a hollow body 10 having enlarged opposed ends 12 and 14 and a narrowed central region 16. The ends are smoothly rounded. The collector is curved as shown and defines an opening 18 on its inner side which is shaped, together with the curvature of the body of the collector, to fit snugly against the perineal region of a female patient. In order to accommodate different patients, the collector body can conveniently be moulded from a flexible plastics material, and should ideally be disposable.

An air inlet 20 is formed in the first end 14 of the collector, and an outlet 22 for air and urine, which can be connected to a flexible hose or pipe 24, is formed at the other end 12. When the collector is placed against the body of a patient, air flowing into the inlet 20 and out of the outlet 22 entrains urine and carries it away for separation from the air.

In order to enhance the efficiency of urine collection, the central region 16 of the collector is narrowed relative to the ends 12 and 14, effectively defining a venturi in the central region of the collector which is located directly adjacent the patient's urethra in use. The venturi results in an accelerated airflow directly adjacent the urethra, enhancing the efficiency of urine collection.

An elasticated strap 26 is fitted to the end 14 of the collector, which will be uppermost in use, to facilitate attachment of the collector to the patient.

Figure 2:
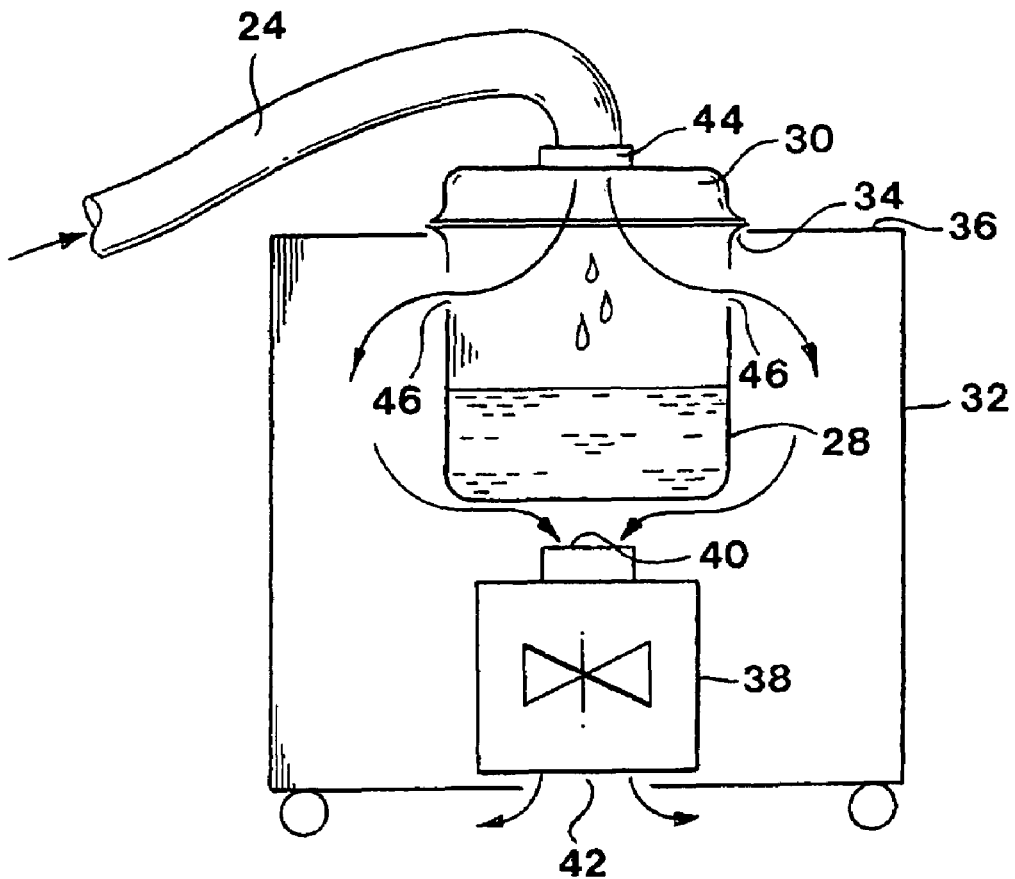
FIG. 2 is a schematic side view of a urine receptacle and low pressure source forming part of the apparatus of the invention.

Referring now to FIG. 2, a urine receptacle comprising a container 28 with a removable lid 30 is shown received in a housing 32. A circular aperture 34 is formed in the upper surface 36 of the housing for this purpose, with the container ideally having an outwardly extending lip to support it in the aperture.

Also located within the housing is a suction source 38 in the form of an impeller arranged to be driven by an electrical motor, and having an air inlet 40 within the housing and an air outlet 42 at the base of the housing. In the prototype apparatus of the invention, the motor/impeller unit from a domestic vacuum cleaner was used.

The container 28 has an inlet 44 for air and urine in the lid 30 thereof and a pair of air outlets 46 formed in the side of the container near the upper rim thereof.

The flexible hose or pipe 24 is connected between the outlet 22 of the urine collector and the inlet 44 of the container as indicated, and the suction source 38 is operated to cause a flow of air through the apparatus as indicated by the arrows in FIGS. 1 and 2. Air with entrained urine is drawn through the hose 24 and the urine drops into the container 28, while the air is drawn through the apertures 46 in the container and exhausted from the bottom of the housing 32. When the container 28 is full, it can simply be lifted out of the housing 32 to be emptied or replaced.

Figure 3:
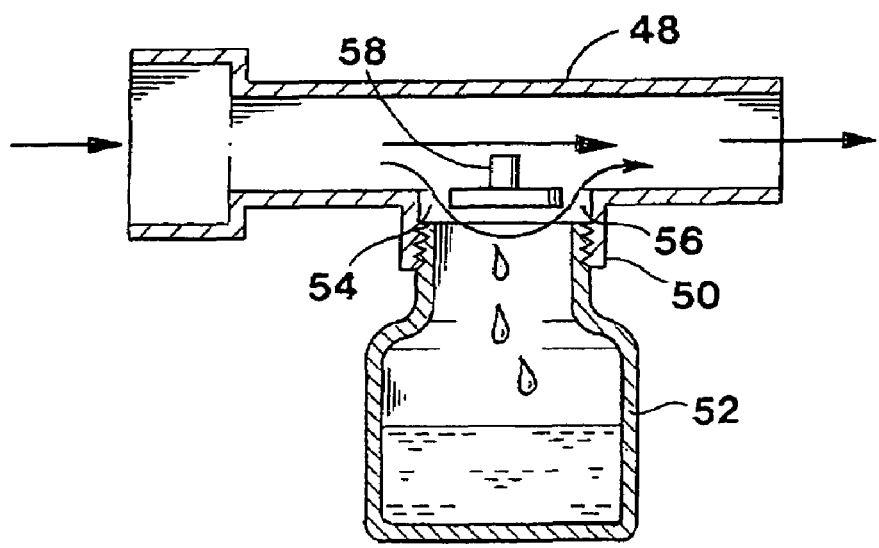
FIG. 3 is a sectional side view of an auxiliary urine sampler of the apparatus.

FIG. 3 shows a urine sampling device which can be used in conjunction with the above described apparatus. It is frequently necessary to take urine samples from patients, and the sampling device was designed to work in conjunction with the above described apparatus to simplify the process.

The sampling device essentially comprises a length of rigid tubing 48 to which sections of hose 24 can be connected. Typically, the sampling device will be connected between the collector 10 and the suction source. The pipe 48 defines a threaded branch 50 into which the neck of a sample bottle 52 can be screwed as indicated. Apertures 54 and 56 are formed in the wall of the pipe 48 in communication with the bore of the branch, and an obstruction in the form of a finger or partition 58 in the pipe between the apertures 54 and 56 causes a portion of the air flowing through the pipe to be diverted through the apertures 54 and 56 as indicated, thereby delivering entrained urine into the container 52.

It will be appreciated that a number of variations of the above described embodiment are possible. For example, the source of low pressure need not be a motor/impeller but could be a steam vacuum line as used in hospitals, or could even be an arrangement making use of a pressure differential such as exists between the interior of an aircraft cabin and the outside atmosphere.

The exact shape and design of the urine collector can also be varied. In practice it was found that it was not essential to maintain an airtight seal between the collector and the body of the patient, and that a degree of air leakage did not impair the functioning of the apparatus.

I claim:

1. A urine collection apparatus comprising:
    a urine collector shaped for location against the perineal region of a patient adjacent the urethra, the urine collector having an inlet for air exposed to an outside of the urine collector and an outlet for air and urine; and
    a urine receptacle having an inlet for receiving air and urine from the urine collector, and an outlet for air which is connectable to a source of low pressure,
    wherein the urine collector is shaped to define a venturi between the inlet and the outlet thereof, the venturi being locatable adjacent the patient's urethra when the urine collector is correctly located, so that air passing through the inlet of the urine collector entrains urine for delivery to the urine receptacle, and
    wherein the inlet for air is visible from outside when the urine collection apparatus is located against the perineal region of the patient.

2. The urine collection apparatus according to claim 1, wherein the urine collector is shaped for use by a female patient.

3. The urine collection apparatus according to claim 1, wherein the urine collector comprises a hollow body having first and second end regions that are opposed to each other and in which the inlet and the outlet are respectively formed,
    the urine collector also having a central region between the first and second end regions having a cross sectional area less than that of the first and second end regions.

4. The urine collection apparatus according to claim 1, wherein the urine collector is formed from a flexible plastics material.

5. The urine collection apparatus according to claim 1, including a source of low pressure in the form of an impeller or pump arranged to apply suction to the outlet of the urine collector when the inlet of the urine receptacle is connected to the outlet of the urine collector, thereby to cause an airflow through the urine collector.

6. The urine collection apparatus according to claim 5, wherein the source of low pressure comprises an impeller arranged to be driven by an electric motor and located in a housing, the urine receptacle being locatable in an opening defined in the housing so that the outlet of the urine receptacle is in communication with an air inlet of the impeller.

7. A urine collection apparatus according to claim 1, wherein the inlet for air is located in an upper wall of the urine collector.

8. A urine collector shaped for location against the perineal region of a patient adjacent the urethra and comprising a hollow body defining an inlet for air exposed to an outside of the urine collector and an outlet for air and urine,
    wherein the body is shaped to define a venturi between the inlet and the outlet thereof, the venturi being locatable adjacent the patient's urethra when the urine collector is correctly located, and
    wherein the inlet for air is visible from outside when the urine collector is located against the perineal region of the patient.

9. The urine collector according to claim 8, wherein the urine collector comprises a hollow body having first and second end regions that are opposed to each other and in which the inlet and the outlet are respectively formed,
    the urine collector also having a central region between the first and second end regions, the central region having a cross sectional area less than that of the first and second end regions.

10. The urine collector according to claim 8, wherein the body is formed from a flexible plastics material.

11. A urine collector being shaped for location against the perineal region of a patient adjacent the urethra and comprising:
    a hollow body defining an inlet for air penetrating through an upper wall of the urine collector; and an outlet for air and urine,
    wherein the body is shaped to define a venturi between the inlet and the outlet thereof, the venturi being locatable adjacent the patient's urethra when the urine collector is correctly located, and
    wherein the inlet for air is visible from outside when the urine collector apparatus is located against the perineal region of the patient.

12. The urine collector according to claim 11, wherein the urine collector comprises a hollow body having first and second end regions that are opposed to each other and in which the inlet and the outlet are respectively formed,
    the urine collector also having a central region between the first and second end regions having a cross sectional area less than that of the first and second end regions.

13. The urine collector according to claim 12, wherein the body is formed from a flexible plastics material.

14. The urine collector comprising the urine collector of claim 11, the urine collection apparatus further comprising:
    a urine receptacle having an inlet for receiving air and urine from the urine collector, and an outlet for air which is connectable to a source of low pressure,
    wherein the air passing through the inlet of the urine collector entrains urine for delivery to the urine receptacle.

15. The urine collector according to claim 14, further comprising an impeller or pump serving as a source of low pressure, the impeller or the pump being arranged to apply suction to the outlet of the urine collector when the inlet of the urine receptacle is connected to the outlet of the urine collector, thereby to cause an airflow through the urine collector.

16. The urine collector according to claim 15, wherein the source of low pressure comprises an electric motor that is located in a housing, the electric motor being arranged for driving the impeller, and
    the urine receptacle being locatable in an opening defined in the housing so that the outlet of the urine receptacle is in communication with an air inlet of the impeller.

* * * * *